(12) United States Patent
Savoia et al.

(10) Patent No.: US 6,178,222 B1
(45) Date of Patent: Jan. 23, 2001

(54) CONTACT MACRORADIOGRAPHY CHARACTERIZATION OF DOPED OPTICAL FIBERS

(75) Inventors: Claudio Savoia; Marziale Milani; Emilia Sottocasa, all of Milan (IT)

(73) Assignee: STMicroelectronics S.r.l., Agrate Brianza (IT)

(*) Notice: Under 35 U.S.C. 154(b), the term of this patent shall be extended for 0 days.

(21) Appl. No.: 09/269,255

(22) PCT Filed: Sep. 19, 1997

(86) PCT No.: PCT/IT97/00229
§ 371 Date: Jun. 1, 1999
§ 102(e) Date: Jun. 1, 1999

(87) PCT Pub. No.: WO98/12544
PCT Pub. Date: Mar. 26, 1998

(30) Foreign Application Priority Data

Sep. 23, 1996 (IT) .................................. VA96A0018

(51) Int. Cl.⁷ ....................................................... G01B 15/06
(52) U.S. Cl. ............................................... 378/58; 378/53
(58) Field of Search ................................. 378/58, 146, 45, 378/147, 157, 53; 350/96.34, 96.29; 250/216, 306, 49.23, 310, 307, 309; 204/192.34

(56) References Cited

U.S. PATENT DOCUMENTS

| 4,616,901 | * | 10/1986 | MacChesney et al. | ........... 350/96.34 |
| 5,093,572 | * | 3/1992 | Hosono | ................................ 250/310 |
| 5,987,092 | * | 11/1999 | Pong | ...................................... 378/36 |

* cited by examiner

Primary Examiner—David P. Porta
Assistant Examiner—Irakli Kiknadze
(74) Attorney, Agent, or Firm—Theodore E. Galanthay; Allen, Dyer, Doppelt, Milbrath & Gilchrist, P.A.

(57) ABSTRACT

The doping of the core of an optical fiber may be precisely characterized by cutting sample slices of the fiber by means of a focused ion beam (FIB) machine and by carrying out a contact radiography of the slices using a soft X-ray source. Maps of the distribution of the dopant ions in the glassy matrix of the optical fiber's core may be obtained by analyzing the contact radiographies at the electronic or atomic force microscope. A dopant concentration value per unit length of fiber may be determined by interpolating the results over a plurality of slices of different thicknesses.

13 Claims, 2 Drawing Sheets

CONTACT MACRORADIOGRAPHY CHARACTERIZATION OF DOPED OPTICAL FIBERS

FIELD OF THE INVENTION

The present invention relates in general to fabrication techniques of optical devices using doped optical fibers and more in particular to methods of testing the doping profiles in the core of an optical fiber.

BACKGROUND OF THE INVENTION

Active optical fibers, typically doped with erbium, are more and more often used in communication systems. In particular the use of erbium doped active optical devices, and specially of erbium doped fiber amplifiers doped is rapidly growing because of the peculiar passband and gain-band characteristics of these devices that favorably coincide with the wavelengths of so-called third window, in the vicinity of 1.5 μm, which is more and more used in optical fiber communication systems.

One of the parameters that most affect doped optical fibers remains the concentration and distribution within the vitreous matrix, generally silicic, of dopant ions, in particular within the core of the optical fiber.

The dopant ions act as active centers similarly to what happens in lasers and therefore their distribution inside the matrix is fundamental in determining the performance of the active optical device.

In optical devices such as fiber amplifiers, the control of the distribution of dopants in the glassy matrix of the core is even more critical because in an optical fiber amplifier the smoothing (levelling) effect of the electromagnetic field due to optical feedback from cavity mirrors does not exist, whereas such effect does exist in lasers.

The article "Chlorine concentration profiles in silica fibers" by H. Hanafusa et al., ELECTRONIC LETTERS, Feb. 16, 1984, UK, vol. 20, no. 4, pages 178–179, and the article "Investigation of the structure of perform materials and fiber-optical waveguides utilizing quartz glass doped with germanium and boron", by A. N. Gur'yanov et al., KVANTOVAYA ELEKTRONIKA, Moskva, October 1979, USSR, vol. 9, no. 10, pages 1238–1242, describe methods for characterizing the doping of the core of an optical fiber and of a preform, respectfully, by x-ray microanalysis. These methods do not provide a direct and reliable distribution pattern of dopant ions on a plane normal to an optical fiber axis.

The determination of the concentration profile, that is, a significatively precise characterization of the doped optical fiber continues to represent a serious problem in view of the difficulty to reliably make such a characterization and this represents a non negligible drawback for the commercial evolution of these technologies.

Until now the characterization is carried out in two different fabrication steps of a doped optical fiber. A first characterization is undertaken on a rod or preform having a diameter of a few centimeters, before the material is drawn in a continuous small diameter fiber. The characterization is made inductively, by exciting the material with a laser and measuring the intensity of the reemission.

However, the drawing process takes place at a temperature of about 800° C. and this inevitably determines a certain diffusion of the doping material during this manufacturing step. Therefore, it is necessary to repeat the characterization on the finished optical fiber, also in this case inductively, and to adapt consequently the length of the active optical fiber in order to attain the required gain value requested by the specifications.

SUMMARY OF THE INVENTION

It is evident the need for a direct characterization method (non inductive) capable of precisely define the doping of an optical fiber core.

A method has now been found, and this is the object of the present invention, to solve this so far elusive problem of directly and reliably analyze the real distribution of dopant ions on a plane normal to the optical fiber, capable of providing a reliable quality control information on the doped optical fiber, as produced, and therefore its intrinsic gain and passband characteristics.

It has now been found that is possible to obtain an optical image of the dopant distribution on a cut fiber portion by means of a soft X-ray Contact Microscopy technique (SXCM).

According to a crucial aspect of the invention it is necessary to prepare sample slices of the optical fiber, thickness of which should be smaller than 20 μm, preferably 10 μm or even less.

With such a sample thickness, the soft X-ray contact microscopy technique can attain reach a resolution of about 50 nm and, by use of proper emission targets and/or of a filter having an appropriate spectral window, it is possible to enhance the contrast between the matrix of silicic glass and, specifically for the particular dopant ions of the core.

According to the method of the invention, the distribution of the relevant dopant ions may be precisely mapped and their total concentration precisely estimated.

According to an important aspect of the invention, the cutting of sample slices with a thickness (or length) in the vicinity of 10 μm, is carried out using a Focused Ion Beam apparatus (FIB).

This type of equipment is described in the article: "Focused Ion Beam", by Jon Orloff, Scientific American, Oct. 1991, pages 74–79.

These equipments are commercially available and they are used in microelectronics generally to perform local modifications or corrections in already fabricated devices, by being able to perform precise cuts and eventually permit to deposit conductive layers of a specific geometry. These equipments are based upon the capacity to generate a beam of strongly accelerated ions that is made to impinge on the sample. The ion beam, which can be precisely focused and guided by means of electrostatic lenses, incides the sample m-aterial being able to dislodge (sputter) ions, electrons and atoms of bombarded surface. Therefore, an FIB may also be used similarly to an SEM, though with inferior resolutions.

The most important characteristic of an FIB is the intrinsic capacity of remarkably restrict the scanning area of the ion beam on the sample surface so to notably increase the density of ion-sample impacts and consequently to attain a major transfer of energy to the sample from the incident particles on an extremely small area.

This energy generates a local microplasma and a consequent ablation of sample material within the impact area of the beam, practically producing obtaining a well defined cavity in the material being bombarded.

The ion beam can be collimated in the order of ten nanometers so that very precise cuts may be performed.

The cutting depth depends solely on the total dose (number of ions per surface unit) of ions impacted onto the scanned zone.

Typically, the ions constituting the primary beam are simply ionized ions of gallium. Gallium possesses only two isotopes with about the same isotopic abundance and is a liquid at ambient temperature. These characteristics permit to obtain a substantially monochromatic and highly energetic beam, because the ionic mass is relatively large, about 70 AMU, and a typical accelerating field is of about 25–30 KeV.

According to a further important aspect of the invention, with a plasma laser source of soft X-rays capable of generating a beam of X-rays with a sufficiently ample diameter, several samples may be simultaneously radiographed, by arranging the samples over an X-ray photoresist layer, disposed on an appropriate support, for example on the bottom of a sample holder which may have a cylindrical shape with a diameter and a height of few millimeters.

A top cover of the cylindrical sample holder may be of silicon nitride ($Si_3N_4$), of about 0.3 to 3 mm thickness. The silicon nitride top cover defines a suitable spectral window through which irradiate the samples placed onto the photoresist support of (e.g. the bottom of the sample holder), thus performing a filtering of the soft X-ray (spectral window), which enhances the contrast between the matrix and the dopants in the irradiated fiber samples.

The sample holder does not need to be evacuated.

A suitable source of soft X-rays may be a plasma laser developed at the Rutheford Appleton laboratory (RAL), Central Laser Facility, (RAL_CLF), which may deliver an average X-ray power of 1 watt at 1 nm wavelength into $2\pi$ steradian, from a point source of a diameter of approximately 10 $\mu$m. The source is constituted by a plasma laser 100 KrF operating in helium at atmospheric pressure. The X-ray beam is focused to 1 mm diameter for a fluence of $10^{12}$ photons/second/mm$^2$, at 100 Hz laser repetition rate, or focused to about 100 nm for a fluence of $10^6$ photons/second/mm$^2$, at 100 Hz laser repetition rate.

The plasma source is excited by a picosecond excimer laser system operating at 248 nm wavelength and delivering a low diffraction beam of trains of 16 pulses, each of 5 ps in length, separated by intervals of 2 ns. The laser energy is of 350 mJ/pulse-train at a repeating rate of up to 100 Hz.

Another example of suitable source of Soft X-rays is the Asterix IV laser system of the Max-Planck Institute fur Quentenoptik. In this case the source is a high power iodine laser photolytically pumped at an emission wavelength of 1,315 um. The Asterix laser system is set in line with a classical Master Oscillator Parametric Amplifier configuration. The pulse to be amplified is either produced by an acousto-optically locked oscillator generating pulses whose duration is less than a nanosecond, or alternatively by a gain switched oscillator, delivering nanosecond pulses. The amplifier chain consists of 6 amplifiers of increasing diameter and length. The final amplifier has an aperture of 29 cm. The Asterix IV laser delivers pulsed length of 0.3 ns, a maximum output power of 4 TW, corresponding to an energy of 1.2 KJ.

While for the RAL-CLF it is necessary to position the samples at only few millimeters from the source, when using a machine having the power characteristics of the Asterix IV it is possible to irradiate the samples at a distance of several centimeters instead of few millimeters thus strongly reducing the penumbral blurring and thereby permitting assessments close to the theoretical limits of resolution.

A further possibility offered by a relatively powerful machine like the Asterix IV is to simultaneously radiate a plurality of sample holders of fiber slices so to increase the production yield of the images and the efficiency and the test statistics.

Of course the spectral window of the X-ray beam may be suitably modified by selecting the nature of the target X emitter in order to enhance the contrast between the matrix and the particular dopant of the core of the fiber.

The dopant ions, excited by the incident X-rays, absorb energy in a more marked and definitely different manner than the surrounding matrix of silicic glass and in the photoresist layer sensible to X-rays a microradiography is obtained which, after the development of the photoresist, may be analyzed using an Atomic Force Microscope (AFM) capable of investigating the image (roughness) produced in the developed layer of photoresist.

The critical parameters of this method of measuring the dose of absorbed X-rays are: the variation of the dopant distribution within the matrix of silicic glass, the sample diameter and its thickness.

Being the X-ray energy expressed in kiloelectrovolt, the resolution is in the order of 70 nm. Therefore, the dopant distribution may be effectively mapped and its concentration estimated.

DETAILED DESCRIPTION OF THE PREFERRED EMBODIMENTS

Figure 1:
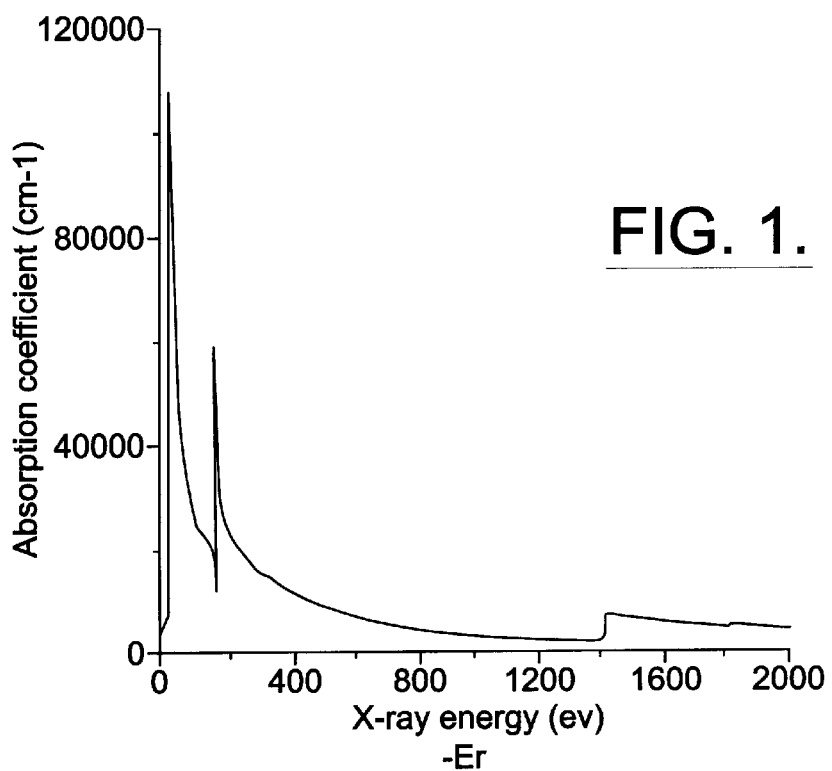
FIGS. 1, 2 and 3 show soft X-rays absorption spectra for Erbium, $SiO_2$ and Pr.
Figure 2:
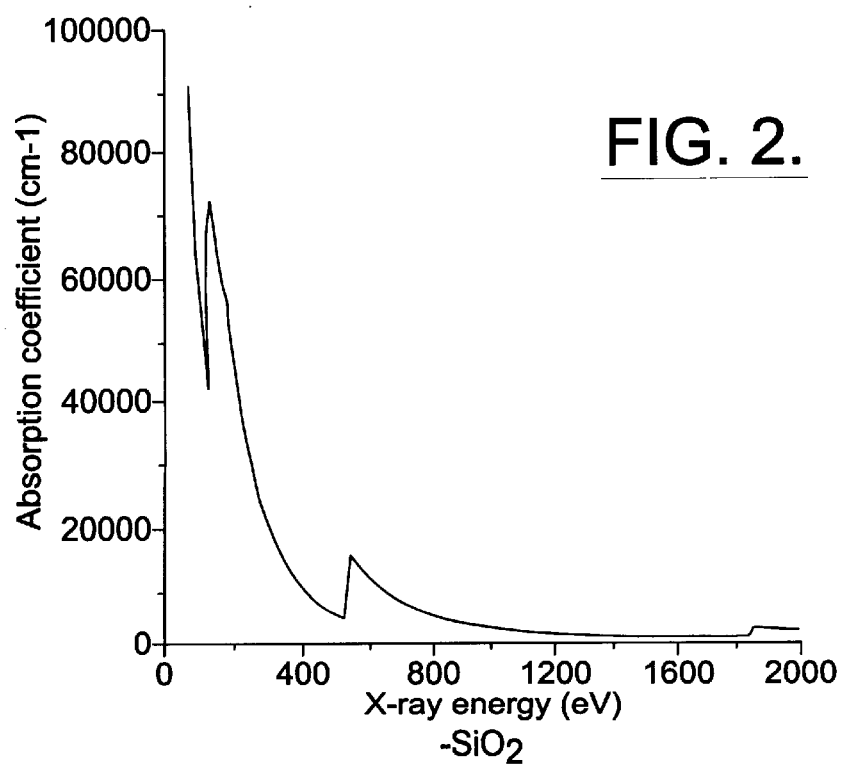
Figure 3:
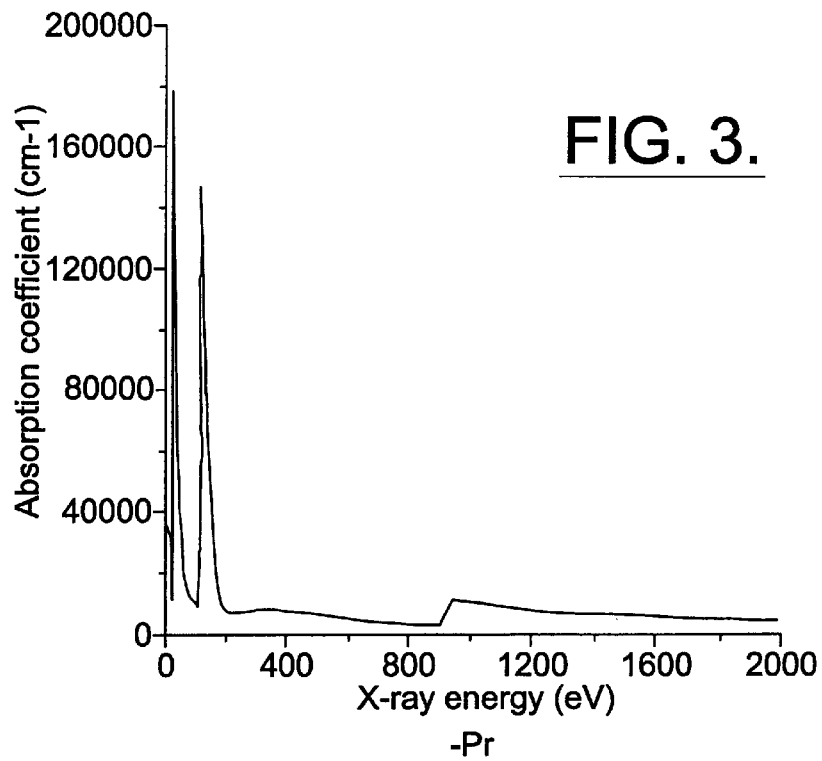

The diagrams showing the absorption for the different materials, that are normally present in the core of the Erbium doped optical fiber, as shown in FIGS. 1, 2 and 3, provide an estimate of the difference between the absorption properties of the respective materials existing in a fiber's core.

Figure 4:
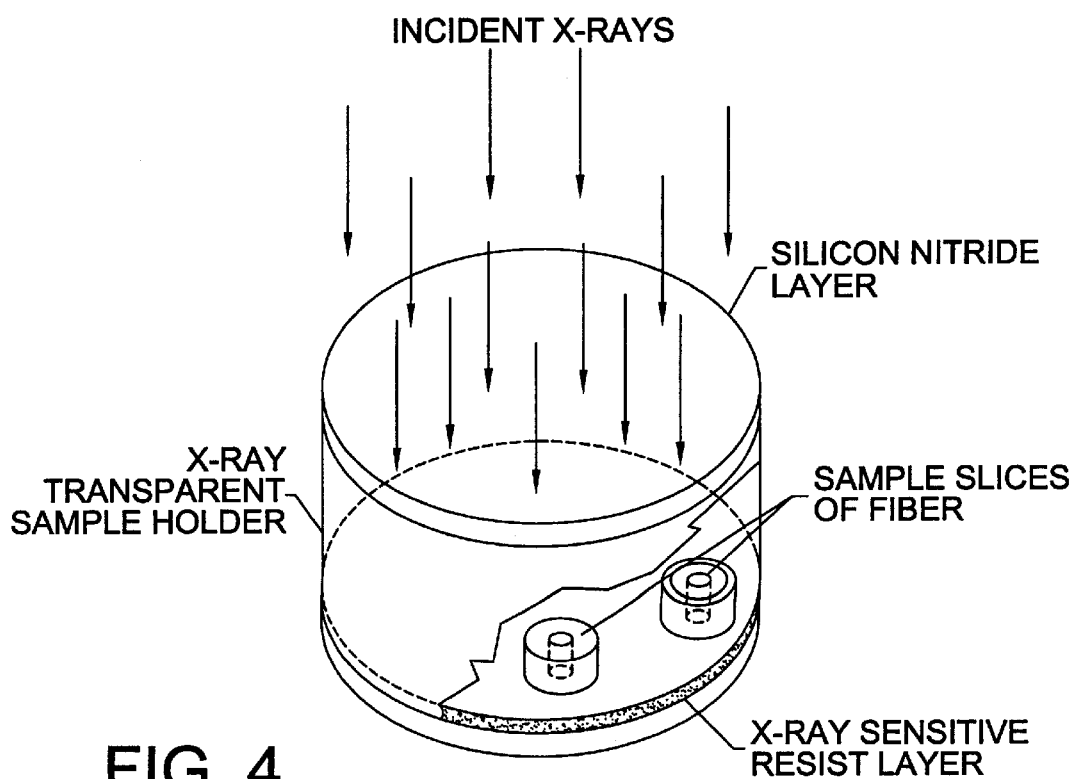
FIG. 4 is a schematic representation of the samples exposure.

FIG. 4 depicts the exposure to the X-ray of the photoresist layer, deposited on a substrate constituting the bottom of a cylindrical sample holder, on the surface of which sample slices of optical fiber, sectioned by a Focus Ion Beams technique, are randomly placed.

The cylindrical sample holder or just the top cover of the cylinder may be either of silicon nitride with a thickness ranging between 0.3 and 3 millimeters or of any other material suitable to define a spectral window effective in enhancing the contrast of the microradiography.

The microradiography thus obtained may be either analyzed with an electronic microscope or an Atomic Force Microscope to determine the dopant concentration based on an integrated measure of the dopant concentration in the whole fiber slice.

Moreover, the method of the invention may also provide a good approximation of the concentration value for an hypothetical slice of infinitesimal thickness, that is, a dopant concentration substantially independent from the thickness of the analyzed fiber slice, in other words a concentration value per unit length of fiber.

This is possible through a characterization undertaken on several sample fiber slices of different length (thickness) of the same fiber and by interpolating the analytical results obtained on samples of different thickness.

This capacity of the method of the invention provides in practice a characterization instrument which allows to model the techniques and thermal treatments for preparing the preforms and drawing them in a highly reproducible manner. In this way it is possible to define a fabrication process which, differently from the known processes, does not require a final calibration test "ad fibram" to ensure that the gain characteristics of a manufactured fiber amplifier meet with the required specifications.

What is claimed is:

1. A method for analyzing the doping of an optical fiber core, the method comprising the steps of:

cutting a sample slice of an optical fiber with a focused ion beam, the sample slice having a thickness not greater than about 20 µm;

placing the sample slice onto a surface of an X-ray photoresist layer disposed on a support;

exposing the sample slice on the photoresist layer to soft X-rays having a wavelength between about 0.5 and 50 nm;

developing the photoresist layer to produce a contact microradiography;

analyzing the contact microradiography produced on the developed photoresist layer with an electron microscope or an Atomic Force microscope; and obtaining a map of the distribution of dopant ions in the optical fiber core.

2. The method according to claim 1, further comprising the step of estimating the concentration of dopant ions in the optical fiber core.

3. The method according to claim 1, wherein the step of exposing the sample slice comprises exposing the sample slice to the soft X-rays through a filter of silicon nitride defining a spectral window of the X-rays.

4. The method according to claim 1, further comprising the steps of:

cutting a plurality of sample slices of the optical fiber, the sample slices having different thicknesses ranging between about 1–20 µm; and interpolating dopant information derived from each sample slice to determine a dopant concentration value per unit length of optical fiber.

5. A method for analyzing the doping of an optical fiber core, the method comprising the steps of:

cutting a sample slice of an optical fiber with a focused ion beam;

disposing the sample slice on a surface of an X-ray photoresist;

exposing the sample slice on the photoresist to X-rays;

developing the photoresist;

analyzing the developed photoresist to derive dopant information of the optical fiber core.

6. The method according to claim 5, wherein the step of developing the photoresist comprises producing a contact microradiography, and further comprising the step of analyzing the contact microradiography produced on the developed photoresist with an electron microscope or an Atomic Force microscope.

7. The method according to claim 5, further comprising the steps of:

obtaining a map of the distribution of dopant ions in the optical fiber core; and estimating the concentration of dopant ions in the optical fiber core.

8. The method according to claim 5, wherein the step of exposing the sample slice comprises exposing the sample slice to soft X-rays through a filter of silicon nitride defining a spectral window of the X-rays.

9. The method according to claim 5, wherein the sample slice has a thickness not greater than about 20 µm.

10. The method according to claim 5, wherein the soft X-rays have a wavelength between about 0.5 and 50 nm.

11. The method according to claim 5, further comprising the steps of:

cutting a plurality of sample slices of the optical fiber, the sample slices having different thicknesses; and interpolating dopant information derived from each sample slice to determine a dopant concentration value per unit length of optical fiber.

12. A method of preparing a sample of an optical fiber, the method comprising steps of:

disposing an optical fiber relative to a focused ion beam device; and cutting a sample slice of the optical fiber using a focused ion beam.

13. The method of claim 12, characterized in that the ions of the focused ion beam are single ionized ions of gallium accelerated in a field of about 25 to 30 KeV.

* * * * *

UNITED STATES PATENT AND TRADEMARK OFFICE
CERTIFICATE OF CORRECTION

PATENT NO.   : US 6,178,222 B1
DATED        : January 23, 2001
INVENTOR(S)  : Claudia Savoia, Marziale Milani, Emilia Sottocasa It is certified that error appears in the above-identified patent and that said Letters Patent is hereby corrected as shown below:

ON THE TITLE PAGE (54), Title

Delete: "MACRORADIOGRAPHY"
Insert --MICRORADIOGRAPHY--

(75), Inventors

Delete: "Milan"
Insert --Milano--

(30), Foreign Application Priority Data

Delete: "VA96A0018"
Insert --VA96A000018--

Column 1, Line 1

Delete: "MACRORADIOGRAPHY"
Insert --MICRORADIOGRAPHY--

Column 2, Line 25

Delete: "technique can attain reach"
Insert --technique can reach--

Column 2, Line 50

Delete: "m-aterial"
Insert --material--

Column 2, Line 54

Delete: "remarkably restrict the"
Insert --remarkably restricting the--

UNITED STATES PATENT AND TRADEMARK OFFICE
CERTIFICATE OF CORRECTION

PATENT NO. : US 6,178,222 B1  
DATED : January 23, 2001  
INVENTOR(S) : Claudia Savoia, Marziale Milani, Emilia Scottocasa Page 2 of 2

It is certified that error appears in the above-identified patent and that said Letters Patent is hereby corrected as shown below:

Column 4, Line 54
        Delete: "value for an"
        Insert --value for a--

Signed and Sealed this

Twenty-ninth Day of May, 2001

*Attest:*

NICHOLAS P. GODICI

*Attesting Officer*      *Acting Director of the United States Patent and Trademark Office*